(12) United States Patent
Jaiswal et al.

(10) Patent No.: US 9,717,800 B2
(45) Date of Patent: *Aug. 1, 2017

(54) FINGOLIMOD CONTAINING STABLE COMPOSITION

(71) Applicant: SUN PHARMACEUTICAL INDUSTRIES LTD., Mumbai (IN)

(72) Inventors: Sunil Jaiswal, Baroda (IN); Krishna Sharma, Baroda (IN); Nitin Bhalachandra Dharmadhikari, Mumbai (IN); Shirish Kulkarni, Baroda (IN)

(73) Assignee: SUN PHARMACEUTICAL INDUSTRIES LTD., Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/842,517

(22) Filed: Sep. 1, 2015

(65) Prior Publication Data

US 2015/0366981 A1 Dec. 24, 2015

Related U.S. Application Data

(63) Continuation of application No. 14/631,335, filed on Feb. 25, 2015, which is a continuation of application No. PCT/IN2014/000030, filed on Jan. 15, 2014.

(30) Foreign Application Priority Data

Jan. 15, 2013 (IN) .......................... 127/MUM/2013

(51) Int. Cl.
*A61K 9/20* (2006.01)
*A61K 9/50* (2006.01)
*A61K 31/125* (2006.01)
*C09K 3/10* (2006.01)
*A61K 47/48* (2006.01)
*A61K 31/137* (2006.01)
*A61K 9/16* (2006.01)
*A61K 47/02* (2006.01)
*A61K 47/12* (2006.01)
*A61K 47/32* (2006.01)

(52) U.S. Cl.
CPC ...... *A61K 47/48184* (2013.01); *A61K 9/1635* (2013.01); *A61K 31/137* (2013.01); *A61K 47/02* (2013.01); *A61K 47/12* (2013.01); *A61K 47/32* (2013.01)

(58) Field of Classification Search
None
See application file for complete search history.

(56) References Cited

U.S. PATENT DOCUMENTS

2010/0040678 A1 2/2010 Ambuhl et al.

FOREIGN PATENT DOCUMENTS

| EP | 2 198 857 A1 | 6/2010 |
| WO | 2008/037421 A2 | 4/2008 |
| WO | 2014/013090 A2 | 1/2014 |

OTHER PUBLICATIONS

International Search Report for PCT/IN2014/000030 dated May 7, 2014.
Written Opinion for PCT/IN2014/000030 dated May 7, 2014.

*Primary Examiner* — Jeffrey T Palenik
(74) *Attorney, Agent, or Firm* — Sughrue Mion, PLLC

(57) ABSTRACT

The present invention relates to a pharmaceutical composition comprising fingolimod and a weak acid cation exchange resin in the form of an ion-exchange complex and pharmaceutically acceptable 5 excipients.

13 Claims, No Drawings

FINGOLIMOD CONTAINING STABLE COMPOSITION

This application is a Continuation of U.S. application Ser. No. 14/631,335 filed Feb. 25, 2015, which is a continuation of International Application No. PCT/IN2014/000030 filed Jan. 15, 2014, claiming priority based on Indian Patent Application No. 127/MUM/2013 filed Jan. 15, 2013, the contents of all of which are incorporated herein by reference in their entirety.

FIELD OF INVENTION

The invention relates to a pharmaceutical composition comprising fingolimod and a weak acid cation exchange resin in the form of an ion-exchange complex and pharmaceutically acceptable excipients. The pharmaceutical composition provides satisfactory chemical stability, adequate content uniformity and desirable rate of dissolution of the active ingredient.

BACKGROUND OF THE INVENTION

Fingolimod, chemically 2-amino-2-[2-(4-octylphenyl)ethyl-]propane-1,3-diol, compound of formula (I), is an S1P receptor agonist. It has been approved for treating multiple sclerosis in USA (trade name GILENYA™) and Russia in 2010 and in Europe, Canada and Australia in 2011.

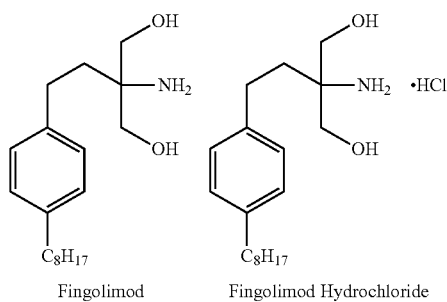

Fingolimod      Fingolimod Hydrochloride

The recommended dose of GILENYA™ is 500 micrograms orally once daily. Fingolimod doses higher than 0.5 mg are associated with a greater incidence of adverse reactions without additional benefit. Fingolimod is a very potent drug and therefore individual units of a dosage form such as capsule or tablets must contain the desired dose of 500 micrograms. It is essential that a low quantity of fingolimod be uniformly distributed in the pharmaceutical excipients that are then filled into capsules or compressed into tablets. Moreover, the fingolimod in the composition must be chemically stable and should be released rapidly from the composition at a desirable dissolution rate. GILENYA™ when tested in of 0.1 N Hydrochloric acid with 1% (w/v) Tween 80 using USP Type II Apparatus rotating at 75 rpm, provides desirable dissolution of more than 80% in 45 minutes.

U.S. Pat. No. 8,324,283 claimed solid pharmaceutical composition for oral administration comprising a S1P receptor agonist such as Fingolimod and a sugar alcohol. The compositions of the invention were to possess good handling physicochemical and storage properties and in particular they provide a high level of uniformity of the distribution of the S1P receptor agonist.

PCT publication, WO2011131368 A2 provided a method of preparing an intermediate comprising (a) fingolimod and (b) one or more pharmaceutically acceptable excipients, comprising the steps of: (i) optionally mixing (a) fingolimod and (b) the excipient or the plurality of excipients, (ii) jointly comminuting (a) fingolimod and (b) the one or more excipients into intermediate particles such that 90 percent by volume of all the resulting intermediate particles have a particle size of less than 250 μms and greater than 0.6 μms. This PCT patent publication explains the invention that the intermediates in the particle size range specified above are particularly advantageous for further use or further processing and that, as a result, a uniform content of active agent, especially in the oral dosage forms based on them, can be achieved. The process taught by the application is well known in the art and is referred to as geometric mixing. We found that the method does not give a high degree of uniformity. Another prior art PCT publication, WO2011131370 A1 provides a method of preparing an intermediate, comprising melt processing (i) fingolimod or a pharmaceutically acceptable salt thereof, with (ii) a matrix former.

SUMMARY OF THE INVENTION

We have found that an ion exchange complex of fingolimod or its pharmaceutically acceptable salt with an ion-exchange resin, such as a cation exchange resin, when formulated into a pharmaceutical composition, provided adequate content uniformity, chemical stability and desirable rate of dissolution of the active ingredient.

DETAILED DESCRIPTION OF THE INVENTION

The present invention provides a pharmaceutical composition comprising fingolimod and a weak acid cation exchange resin in the form of an ion-exchange complex and pharmaceutically acceptable excipients.

As used herein, unless indicated otherwise, references to fingolimod include fingolimod in its free base form, or as any one of it's pharmaceutically acceptable salt. Fingolimod or its pharmaceutically acceptable salt, used in the present invention is chemically known as 2-amino-2-(2-[4-octylphenyl)ethyl]-1,3-propanediol. It is also commonly referred to as FTY720. Its pharmaceutically acceptable salts used herein include, but are not limited to, hydrochloride, carbonate, hydrogen carbonate, acetate, lactate, butyrate, propionate, sulphate, methane sulphonate, citrate, tartrate, nitrate, sulphonate, oxalate and succinate. In illustrative examples of the present invention, hydrochloride salt of Fingolimod is used. The amount of fingolimod or its pharmaceutically acceptable salt used in a single unit dosage form according to the present invention ranges from about 0.10 mg to about 2.5 mg; preferably from about 0.125 mg to about 1.25 mg; from about 0.25 mg to about 1.0 mg; from about 0.25 mg to about 0.75 mg; from about 0.25 mg to about 0.50 mg; from about 0.1 mg to about 0.5 mg; from about 0.125 mg to about 0.5 mg; preferably about 0.125 mg, most preferably about 0.5 mg per unit dosage form.

The term 'ion-exchange complex' as used herein, can be interchangeably used with the term 'ion-exchange resinate' or 'drug resinate' or 'drug-ion exchange resinate' or 'drug-ion exchange resin complex' or 'drug-resin complex' or 'ion exchange resin complex". It refers to substances that are insoluble polymers that contain either acidic or basic functional groups and have the ability to exchange counter-ions within aqueous solutions surrounding them. Based on the nature of the exchangeable ion of the resin as a cation or anion, it is classified as cationic or anionic exchange resins, respectively. They differ in the ionizable group attached to the hydrocarbon network. It is this functional group that determines the chemical behavior of the resin. Cation exchange resins are polymers that contain appropriately substituted acidic groups, such as carboxylic and sulfonic; and the anion exchange resins are polymers that contain basic groups, such as primary, secondary or tertiary amines or quaternary ammonium group. Resins can be further classified as strong or weak acid cation exchange resin or strong or weak base anion exchange resin. Strong acid cation exchange resins are so named because their chemical behavior is similar to that of a strong acid. These resins are highly ionized. In a weak acid cation exchange resin, the ionizable group is a weakly acidic group such as carboxylic acid (COOH). These resins behave similarly to weak organic acids that are weakly dissociated. Ion exchange resins are available by various manufactures and are known by their trade names such as Amberlite or Duolite (by Rohm & Haas Company); Dowex (by Dow Chemical Company); Indion (by Ion Exchange India Ltd.); Tulsion (by Thermax Chemicals ltd. India); Purolite (by Purolite USA); Doshion (by Doshion Limited, India).

As used herein, the term 'content uniformity' or uniformity of content can be used interchangeably. Content Uniformity can be determined by the procedure provided in United States Pharmacopoeia (USP) 34. According to USP, the acceptance value of the 10 individually tested units should be equal or less than L1, where L1 is 15. Lesser the value of L1, better is the uniformity of drug content. If the dosage form does not comply with this criteria then additional 20 dosage units are individually tested and L2 is determined and its value should be less than or equal to 25.

The term 'stable' as used herein means that the pharmaceutical composition is chemically stable in terms of assay of the drug and the limits of known and unknown impurities or decomposition products, under storage conditions defined in the ICII guidelines. ICII guidelines provides that a composition is said to be stable when the individual known impurities are below 0.1% and the total impurities are below 1.0% over the shelf life of the drug product. According to the present invention, the individual known impurities for fingolimod that should be less than 0.1% are as referred to as Impurity A, Impurity B and impurity C and their chemical names are given below: Impurity A: N-[1,1-Bis-hydroxymethyl-3-(4-octyl-phenyl)-propyl]-acetamide; Impurity B: 2-Acetylamino-2-[2-(4-octyl-phenyl)-2-oxo-ethyl]-malonic acid diethyl ester; Impurity C: N-[1-Hydroxymethyl-3-(4-octyl-phenyl)-propyl]-acetamide. The identification and quantification of the known and unknown impurities is done by standard methods such as HPLC.

The present invention provides a pharmaceutical composition comprising fingolimod and a weak acid cation exchange resin in the form of an ion-exchange complex and pharmaceutically acceptable excipients.

Preferred embodiments of the present invention provide a pharmaceutical composition comprising fingolimod and a weak acid cation exchange resin in the form of an ion-exchange complex wherein the weak acid cation exchange resin is a copolymer of methacrylic acid and divinylbenzene as depicted by Formula I:

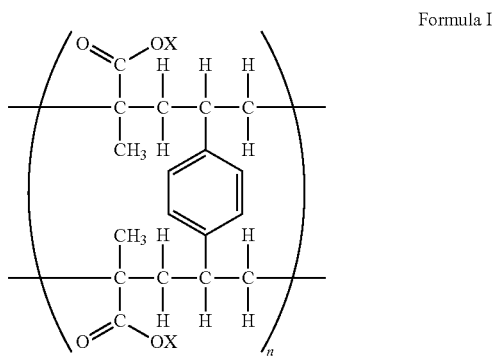

Formula I wherein X is hydrogen or an inorganic monovalent cation.

Examples of weak acid cation exchange resin, that are used according to the present invention, include, but are not limited to, a cross-linked polymer of methacrylic acid and divinylbenzene of Formula I. Weak acid cation exchange resin of Formula I is official in National Formulary, USP 23/NF18. It is commercially manufactured by many companies. For example, it is commercially available under the tradename, Amberlite IRP88®. It is also commercially available under the tradename, Indion® 294. On the other hand, the weak acid cation exchange resin of Formula I, wherein X is a hydrogen ion, is available commercially under the tradename, Amberlite® IRP64® or Indion® 264.

In one embodiment, the present invention provides a pharmaceutical composition comprising fingolimod and a weak acid cation exchange resin in the form of an ion-exchange complex, wherein the weak acid cation exchange resin is as depicted in Formula I wherein X is $H^+$ (hydrogen ion). In another embodiment, the present invention provides a pharmaceutical composition comprising fingolimod and a weak acid cation exchange resin in the form of an ion-exchange complex, wherein the weak acid cation exchange resin is as depicted in Formula I wherein X is an inorganic monovalent cation such as $K^+$, $Na^+$ and the like.

In a preferred embodiment, the present invention provides a pharmaceutical composition comprising fingolimod and a weak acid cation exchange resin in the form of an ion-exchange complex, wherein the weak acid cation exchange resin is as depicted in Formula I, and wherein the weight ratio of fingolimod to the weak acid cation exchange resin ranges from about 1:1 to about 1:10 by weight, preferably about 1:3 to about 1:10 by weight. Particularly, the weight ratios of fingolimod to the weak acid cation exchange resin may be any ratio in the range of about 1:3 to about 1:10, for instance it may be 1:3 or 1:4 or 1:5 or 1:6 or 1:7 or 1:8 or 1:9 or 1:10. It is to be noted that the ratios specifically are determined with reference to fingolimod as the fingolimod hydrochloride salt but the term 'about' is used to encompass the variation in ratios observed when different salts of Fingolimod as against the fingolimod hydrochloride are used. Thus the ratio of 1:3 means for 1 g of fingolimod hydrochloride there is 3 g of weak cation exchange resin, but if computed with reference to the base then the ratio is 1:3.36. It was found that as the proportion of resin increased, the content uniformity and chemical stability of the composition improved. Thus, drug: resin weight ratios greater than about 1:3 are preferred, more preferably the ratios greater than about 1:6.

In one particularly preferred embodiment, the present invention provides a pharmaceutical composition comprising fingolimod and a weak acid cation-exchange resin in the form of an ion-exchange complex, wherein the weak acid cation exchange resin is as depicted in Formula I wherein X is potassium and wherein the weight ratio of fingolimod to the weak acid cation exchange resin is about 1:6 by weight. In one embodiment, it was found that for the weak acid cation exchange resin as depicted in Formula I wherein X is a hydrogen ion, 100% complexation of the drug took place at a weight ratio of fingolimod to the resin of about 1:10.

In one embodiment, the present invention provides a pharmaceutical composition comprising fingolimod and a weak acid cation exchange resin in the form of an ion-exchange complex, wherein the weak acid cation exchange resin is as depicted in Formula I, wherein X is hydrogen and wherein the weak acid cation exchange resin have an ion exchange capacity of not less than 10.0 meq/g on dried basis, wherein the mean particle size of the resin particles lies in the range of about 150 micron to about 45 micron and wherein the particle size distribution of the resin is such that not more than 70% of particles have a particle size greater than about 50 micron; 15% to 30% of the particles have a particle size of greater than about 75 micron and not more than 1% of the particles have a particle size of greater than about 150 micron.

In another aspect, the present invention provides a pharmaceutical composition comprising fingolimod and a weak acid cation-exchange resin in the form of an ion-exchange complex, wherein the weak acid cation exchange resin is as depicted in Formula I, wherein X is a potassium ion and wherein the weak acid cation exchange resin is such that the mean particle size of the cation exchange resin lies in the range of about 150 micron to about 45 micron and wherein the particle size distribution of the resin is such that not more than 30% of the particles have a particle size in the range of about 75 micron to about 150 micron; not more than 1% of the particles have a particle size of greater than about 150 micron.

The pharmaceutical composition of the present invention may be prepared by first preparing an ion-exchange complex of Fingolimod with the weak acid cation exchange resin and then mixing the ion-exchange complex with pharmaceutically acceptable excipients. The composition may be converted into a suitable dosage form. The ion-exchange complex may be mixed with other excipients in the form of its suspension or alternatively it may first be dried and then mixed with other excipients. More particularly the process comprises the following steps:
(a) Dissolve Fingolimod in the form of its salt in water.
(b) Add the weak acid cation exchange resin to obtain a suspension
(c) Add the suspension obtained in (b) to pharmaceutically acceptable excipients to form granules
(d) Dry the granules and convert them into a suitable dosage form by conventional means.

Preferably, the process for preparing a pharmaceutical composition of the present invention comprises the below steps—
(a) Dissolve fingolimod in the form of its salt in water;
(b) Add the weak acid cation exchange resin to obtain a suspension
(c) Dry the suspension of step (b) to obtain a dry ion-exchange complex
(d) Mix the ion-exchange complex of step (c) with pharmaceutically acceptable excipients and convert them into a suitable dosage form.

Preferably the drying step (c) may be carried out by applying vacuum and high temperature of about 60° C.

According to one embodiment of the present invention, the pharmaceutical composition comprises fingolimod in an amount ranging from about 0.1% to about 2% by weight of the total composition; the weak acid cation-exchange resin in an amount ranging from about 0.1% to about 10% by weight and pharmaceutically acceptable excipients in an amount ranging from about 0.1% to about 90% by weight of the total composition.

According to one preferred embodiment of the present invention, the pharmaceutical composition comprises fingolimod in an amount ranging from about 0.1% to about 1.0% by weight of the total composition; the cation-exchange resin in an amount ranging from about 1% to about 8% by weight of the total composition and pharmaceutically acceptable excipients in an amount ranging from about 1.0% to about 90% by weight of the total composition.

The pharmaceutical compositions of the present invention are provided in the form of oral solid dosage forms such as a tablet; capsule; granules, orally disintegrating tablets, bilayered tablets, inlay tablets; powder filled into capsule or compressed into a tablet; granules filled into capsule or compressed into a tablet; or any other suitable solid oral dosage forms. The dosage forms may further comprise one or more of other pharmaceutically acceptable excipients depending on the dosage form to be formulated. Pharmaceutically acceptable excipients may include, without limitation, diluents; binders; lubricants/glidants; disintegrants; buffer systems; sweetening agents; flavoring agents; coloring agents; solvents/co-solvents and the like.

Suitable diluents that may be used include, but are not limited to microcrystalline cellulose, crospovidone, microcrystalline cellulose, microfine cellulose, lactose, starch, pregelatinized starch, calcium carbonate, calcium sulfate, sugar, mannitol, sorbitol, dextrates, dextrin, maltodextrin, dextrose, dibasic calcium phosphate dihydrate, tribasic calcium phosphate, magnesium carbonate, magnesium oxide, as well as other conventional diluents well known to the persons skilled in the art.

Suitable binders that may be used include, but are not limited to, acacia, guar guru, alginic acid, carbomer, dextrin, maltodextrin, methylcellulose, ethyl cellulose, hydroxyethylcellulose, hydroxypropylcellulose, hydroxypropylmethylcaulose, carboxymethylcellulose sodium, magnesium aluminum silicate, polymethacrylates, crospovidones, povidones, copovidones, gelatin, starch as well as other conventional binders well known to the persons skilled in the art.

Suitable lubricants/glidants that that may be used include, but are not limited to, magnesium stearate, zinc stearate, calcium stearate, stearic acid, colloidal silicon dioxide, glycerylpalmitostearate, vegetable oils, polyethylene glycols, polyvinyl alcohols, talc, sodium benzoate, sodium stearyifurnarate, magnesium oxide, poloxamer, sodium lauryl sulphate, polyoxyethylenemonostearate, cocoa butter, hydrogenated vegetable oils, mineral oil, polysaccharides as well as other conventional lubricants/glidants well known to the persons skilled in the art.

Suitable disintegrants and/or superdisintegrants that may be used in the present invention include, but are not limited to crospovidone, croscarmellose sodium; sodium starch glycolate; polyvinylpyrrolidone; carboxymethylcellulose and the like. Other suitable disintegrants that may be used, include mannitol, alginic acid, hydroxypropylcellulose, microcrystalline cellulose, methylcellulose, sodium alginate, starch and other similar agents well known to the persons skilled in the art.

Suitable buffer systems include, but are not limited to, sodium hydroxide, acetic, boric, carbonic, phosphoric, succinic, maleic, tartaric, citric, benzoic, lactic, glyceric, gluconic, glutaric and glutamic acids and their sodium, potassium and ammonium salts, as well as other conventional buffer systems well known to the persons skilled in the art.

Suitable taste-masking agents that may be used include flavors and sweeteners. Flavors may be chosen from natural and synthetic flavor liquids and include, but are not limited to, volatile oils, synthetic flavor oils, flavoring aromatics, oils, liquids, oleoresins or extracts derived from plants, leaves, flowers, fruits, stems and combinations thereof. The sweeteners may be chosen from the following non-limiting list: sucrose, dextrose, invert sugar, fructose, and mixtures thereof, saccharin, aspartame, acesulfame, sucralose, sugar alcohols such as sorbitol, mannitol, xylitol, and the like.

Suitable coloring agents include, but are not limited to, titanium dioxide pigments, lake colors, iron oxide pigments, and the like.

Suitable solvents and/or co-solvents that may be used for several purposes include, but are not limited to, water, ethanol, organic polar and non-polar solvents, glycerin, propylene glycol, polyethylene glycol and their suitable mixtures.

According to one particularly preferred embodiment of the present invention, the pharmaceutical composition is in the form of hard gelatin capsule, filled with ion-exchange resin complex of fingolimod hydrochloride with a weak acid cation-exchange resin and pharmaceutically acceptable excipients. In one specific embodiment, the pharmaceutical composition comprise diluents such as crospovidone NF/Ph.Eur. (also called Polyplasdone XL) and lubricants such as colloidal silicon dioxide NF (or Colloidal anhydrous silica Ph. Eur.) or magnesium stearate. The pharmaceutical composition according to this embodiment, comprises fingolimod hydrochloride in an amount of about 0.62% by weight; the weak acid cation-exchange resin Amberlite IRP64 in an amount of about 1.87% by weight and crospovidone in an amount of about 50% by weight and lubricant such as colloidal silicon dioxide and magnesium stearate, each in an amount of 0.55% by weight of the total composition.

According to another specific embodiment, the present invention provides a pharmaceutical composition in the form of a capsule, wherein the composition comprises fingolimod hydrochloride in an amount of about 0.62% by weight of the total composition; the cation-exchange resin Amberlite IRP 88, in an amount of about 4.98% by weight and crospovidone in an amount of about 50% by weight of the total composition.

Suitable methods may be employed for the evaluation of degree of complexation of the drug with resin. Particularly, the free drug content, the complexed drug content and total drug content may be estimated by a method of analysis employing High Performance Liquid Chromatography (HPLC). According to one embodiment of the present invention, the percentage free drug; the percentage complexed drug and total drug content may be determined and analyzed by the method described herein below:

Specified amount of the ion-exchange resin complex was weighed accurately and transferred into a 200 ml volumetric flask. About 150 ml of water was added to the granules and the mixture was sonicated for about 20 min with intermittent shaking and the volume was made up to the mark with water. The admixture was mixed well and the whole 200 ml solution was centrifuged without wasting anything at 4000 rpm for 15 min. The clear supernatant so obtained contains the free drug (un-complexed non-resinate part). A sample of the supernatant was analyzed through a suitable HPLC method to obtain the free drug content. The residue part contains the complexed drug. To analyze the complexed drug, the sample was processed further as below:

Method of Estimation of Complexed Fingolimod Content

The sample as obtained above was processed further to determine the complexed drug content.

The clear supernatant was carefully discarded. To ensure removal of the entire free drug content, about 10 ml of water was again added to the residue and centrifugation was carried out at 4000 rpm for 15 mins. The clear supernatant was carefully discarded. The remaining residue is the ion-exchange complex containing the complexed drug. To analyze the complexed drug, 0.1 N Hydrochloric acid was added to the residue with vortexing and heating in a water bath maintained at 37° C. for 30 mins. The liquid part was then collected in a separate 200 ml volumetric flask. The residue container was washed at least twice with a diluent* and the washings were collected into the same 200 ml volumetric flask. With intermittent shaking, the solution was sonicated for about 20 minutes. The solution was allowed to cool to room temperature and the volume was made up with the diluent*, followed by proper mixing and centrifugation at 4000 rpm for 15 min to get clear supernatant. This clear supernatant contains the complexed drug. A sample of the supernatant was analyzed through a suitable HPLC method to obtain the complexed drug content.

Method of Estimation of Total Fingolimod Content

The ion-exchange resin complex was weighed accurately and transferred into a 200 ml volumetric flask. Measured volume of 0.1 N hydrochloric acid was added to this. The flask was heated into water bath maintained at 37° C. for about 30 min with intermittent shaking. The solution was then cooled and A mixture of buffer (potassium dihydrogen orthophosphate/orthophosphoric acid buffer) and acetonitrile in the ratio of 30:70 was added followed by sonication for about 20 min with intermittent shaking. The volume up made up to the mark with the above buffer mixture, mixed well and centrifuged at 4000 RPM for 15 minutes. The clear supernatant contains the total drug. A sample of the supernatant was analyzed through a suitable HPLC method to obtain the total drug content (as % of L.C.).

The pharmaceutical composition of the present invention is 'stable' in terms of assay of the drug and the limits of known and unknown impurities/decomposition products under standard storage conditions. Stability characteristics may be determined, for e.g. by measuring the impurities or decomposition products by HPLC analysis or any other suitable method, after storage for particular times and at particular temperatures and humidity conditions e.g. 25° C./60% Relative Humidity (RH), 30° C./65% RH or 40° C./75% RH, (also called as accelerated stability studies) as specified by the regulatory authorities or as per ICH guidelines.

The individual impurities identified and known for Fingolimod hydrochloride are—

Impurity A: N-[1,1-Bis-hydroxymethyl-3-(4-octyl-phenyl)-propyl]-acetamide

Impurity B: 2-Acetylamino-2-[2-(4-octyl-phenyl)-2-oxo-ethyl]-malonic acid diethyl ester Impurity C: N-[1-Hydroxymethyl-3-(4-octyl-phenyl)-propyl]-acetamide The pharmaceutical compositions of the present invention were subjected to accelerated stability testing and it was found that the individual known impurities (A, B, C); the highest unknown impurity and the percent total impurity levels remained within acceptable limits. Particularly, the level of individual impurities A, B and C when subjected to accelerated stability studies at 40° C./75% relative humidity remained below 0.1% even after 6 month of the study. Further, the level of % total impurity remained below 1.0% after 3 month of the study. This indicated that the pharmaceutical composition of the present invention possessed excellent stability characteristics and shall remain stable for the shelf life of the product. On the other hand, it was found that the impurities levels were very high for the composition without weak acid cation exchange resin. For example, the comparative example 2, showed the total impurities as high as 3.2%, at the end of shelf life.

Hereinafter, the invention will be more specifically described with reference to examples. The examples are not intended to limit the scope of the invention and are merely used as illustrations. Certain modifications and equivalents will be apparent to those skilled in the art and are intended to be included within the scope of the invention.

Comparative Example 1

TABLE 1

| Composition of fingolimod without weak acid cation exchange resin | | |
|---|---|---|
| Ingredients | mg per capsule | % w/w |
| Fingolimod hydrochloride | 0.56 | 0.62% |
| Crospovidone | 48.44 | 53.82% |
| Colloidal silicon dioxide | 1.00 | 1.11% |
| Hard gelatin capsules size "4" | 40.00 | 44.44% |

Fingolimod hydrochloride was geometrically mixed with the excipients and filled into capsules. This was similar to the method described in a prior art, PCTWO2011131368 A2.

The content uniformity of the capsules was determined by the procedure provided in United States Pharmacopoeia 34. According to USP, the acceptance value of the 10 individually tested units should be equal or less than L1, where L1 is 15. Lesser the value of L1, better is the uniformity of drug content. If the dosage form does not comply with this criteria then additional 20 dosage units are individually tested and L2 is determined and its value should be less than or equal to 25.

The results of the content uniformity for composition provided in comparative example are indicated in Table 2(a).

TABLE 2(a)

| Results of the content uniformity of comparative example | | |
|---|---|---|
| Batch No. | Assay values | Acceptance value (Limit: L1 ≤15 and L2 ≤25) |
| 1 | Mean 105.09%, Min: 100.15%, max: 110.64%, % RSD = 2.95 | 11.03 |
| 2 | Mean 102.91%, Min: 94.87%, max: 109.33%, % RSD = 4.12 | 11.59 |

Table 2(a) indicates poor uniformity of drug content as indicated by acceptance value as the latter values although within limit were on the higher side closer to 15. The capsules of comparative example 1 were subjected to the accelerated stability testing and the results are provided in Table 2b.

TABLE 2(b)

| Stability Study Result of Comparative Example 1 | | | | |
|---|---|---|---|---|
| | | 40°/75 RH | | 30°/65% RH |
| Parameters | Initial | 1 month | 6 month | 3 month |
| Assay | 106.6 | 103.9 | 104.58 | 106.9 |
| % Single highest unknown impurity | 0.27 | 0.274 | 0.66 | 0.42 |
| % Total impurity | 0.27 | 0.408 | 1.39 | 0.726 |

Comparative Example 2

TABLE 3

| Composition of fingolimod without weak acid cation exchange resin | | |
|---|---|---|
| Ingredients | mg per capsule | % w/w |
| Fingolimod hydrochloride | 0.56 | 0.16% |
| Dibasic calcium Phosphate | 281.94 | 80.0% |
| Polyvinylpyrrolidone | 6.0 | 1.7% |
| Colloidal silicon dioxide | 1.5 | 0.43% |
| Hard gelatin capsules size "2" | 62 | 17.61% |

Fingolimod hydrochloride was geometrically mixed with the excipients and filled into capsules. This was similar to the method described in a prior art, PCTWO2011131368 A2.

The capsules of comparative example 2 were packed in Aluminum/Aluminum blister and were subjected to accelerated stability studies at various test conditions (40° C./75% RH, 30° C./65% RH). The study was continued for 3 months to check the long term stability of the formulation. The samples were analyzed for assay of the drug, percent single highest impurity and percent total impurity. The results of the stability studies are given below in Table 4.

TABLE 4

Stability Study Result of Comparative Example 2

| Parameters | Initial | 40/75% RH | | | 30/65% RH |
| --- | --- | --- | --- | --- | --- |
| | | 1 month | 2 month | 3 month | 3 month |
| Assay | 102.53 | 91.06 | 90.68 | 85.32 | 101.66 |
| % Single highest unknown impurity | 0.044 | 0.142 | 0.443 | 0.689 | 0.153 |
| % Total impurity | 0.146 | 0.542 | 1.683 | 3.200 | 0.509 |

From the above stability data, it was observed that the comparative composition of Example 2 is unstable and the drug undergoes degradation upon storage wherein a high percent total impurity of 3.2% was observed after 3 Month when kept at 40° C./75% relative humidity (RH).

Example 1

The example illustrates a composition of the present invention comprising the ion-exchange resin of Formula 1, wherein X is hydrogen and ratio of fingolimod base to resin is 1:3.36 or ratio of fingolimod hydrochloride to resin is 1:3.

TABLE 5

Pharmaceutical composition using Amberlite IRP64

| Sr. No. | Ingredients | mg/capsule | % w/w |
| --- | --- | --- | --- |
| | Step 1: Complexation | | |
| 1 | Fingolimod Hydrochloride equivalent to 0.5 mg Fingolimod base | 0.56 | 0.62 |
| 2 | Amberlite IRP 64 | 1.68 | 1.87 |
| 3 | Purified water | q.s. | |
| | Step 2: Granulation | | |
| 1 | Crospovidone | 46.76 | 51.95 |
| | Step 3: Blending and lubrication | | |
| 1 | Colloidal silicon dioxide | 0.50 | 0.55 |
| 2 | Magnesium stearate | 0.50 | 0.55 |
| | Step 4: Encapsulation | | |
| 1 | Hard Gelatin Capsule, Size "4" | 40.00 | 44.4 |

Fingolimod hydrochloride was dissolved in water. Weak acid cation exchange resin was added to the drug solution and the dispersion was stirred for three hours. The dispersion was used to granulate crospovidone as the diluent in a suitable shear granulator. The granules were dried in a suitable dryer. The dried granules were blended with colloidal silicon dioxide and magnesium stearate in a suitable blender. The lubricated blend was encapsulated in hard gelatin capsules (fill weight 50 mg per capsule for 0.5 mg active strength). The resulting composition was checked for content uniformity. The results are given below in Table 6.

TABLE 6

Results of the content uniformity of pharmaceutical composition of example 1

| Assay values | Acceptance value (Limit: L1 ≤15 and L2 ≤25) |
| --- | --- |
| Mean 102.47%, Min: 97.8%, max: 106.52%, % RSD = 2.63 | 7.43 |

Table 6 is indicative of improved content uniformity as reflected by lower acceptance value as compared to the composition of comparative example 1.

The pharmaceutical composition (capsules) of Example 1 were packed in Alu-Alu blister and were subjected to accelerated stability studies at various test conditions (40° C./75% RH, 30° C./65% RH; 25° C./60% RH). The study was continued for 6 months to check the long term stability of the formulation. The samples were analyzed for assay of the drug, impurity levels and total impurity. The results of the stability study are given in table 7 below:

TABLE 7

Results of the chemical stability of pharmaceutical composition of example 1

| Parameters | Initial | 40/75% RH | | | 30/65% RH | | | 25/60% RH | | |
| --- | --- | --- | --- | --- | --- | --- | --- | --- | --- | --- |
| | | 1 M | 3 M | 6 M | 1 M | 3 M | 6 M | 1 M | 3 M | 6 M |
| Assay | 104.12 | 102.54 | 97.85 | 94.37 | 102.21 | 103.22 | 96.81 | 101.23 | 103.19 | 100.09 |
| Dissolution** at 45 mins | 101 | 92 | 88 | 83 | 96 | 92 | 86 | 94 | 89 | 89 |
| Impurity A | ND | 0.008 | 0.024 | 0.018 | 0.001 | 0.005 | 0.004 | ND | 0.002 | ND |
| Impurity B | ND | ND | ND | ND | ND | ND | 0.014 | ND | ND | 0.010 |
| Impurity C | ND | ND | ND | ND | ND | ND | ND | ND | ND | ND |
| % Highest unknown impurity | 0.082 | 0.127 | 0.262 | 0.353 | 0.108 | 0.105 | 0.131 | 0.099 | 0.080 | 0.135 |
| % Total impurity | 0.200 | 0.604 | 1.084 | 1.223 | 0.340 | 0.405 | 0.668 | 0.299 | 0.296 | 0.454 |
| Disintegration time | 3.45 | 2.83 | 3.42 | 2.92 | 2.97 | 3.09 | 2.61 | 2.97 | 2.89 | 2.57 |
| Water content | 9.636 | 15.621 | 12.221 | 19.275 | 11.186 | 14.018 | 11.926 | 10.123 | 12.593 | 13.469 |

M = month

ND = not detectable;

**= USP Type II Apparatus(Paddle with sinkers) at 75 rpm, in 500 ml of 0.1N Hydrochloric acid with 1% (w/v) Tween 80

Upon comparing the impurities levels of Example 1 and the comparative example 1 and 2, it was observed that % total impurity observed after six months when kept at 40° C./75% Relative Humidity, for the comparative example 1 was 1.39%, the % total impurity observed after three months when kept at 40° C./75% Relative Humidity, for the comparative example 2 was 3.2%. In contrast, total impurity for example 1 were considerably low, i.e about 1%. Moreover, it was observed when capsules were stored for six months, the % total impurity increased nominally to 1.223% from 1.0% (refer to Table 7). Thus, it is very evident from the data that pharmaceutical composition of Example 1 using weak acid cation exchange resin like Amberlite IRP64, no significant impurities were formed as against compositions without weak acid cation exchange resin.

Example 2

The example illustrates a composition of the present invention comprising the ion-exchange resin of Formula 1, wherein X is potassium and ratio of fingolimod base to resin is 1:8.96 or ratio of fingolimod hydrochloride to resin is 1:8.

TABLE 8

Pharmaceutical composition using Amberlite IRP88

| Sr. No. | Ingredients | mg/capsule | % w/w |
|---|---|---|---|
| | Step 1: Complexation | | |
| 1 | Fingolimod Hydrochloride equivalent to 0.5 mg Fingolimod base | 0.56 | 0.62% |
| 2 | Amberlite IRP 88 | 4.48 | 4.98% |
| 3 | Purified water | q.s. | |
| | Step 2: Granulation | | |
| 1 | Crospovidone | 44.96 | 49.95% |
| | Step 3: Encapsulation | | |
| 1 | Hard Gelatin Capsule, Size "4" | 40.00 | 44.44% |

Fingolimod hydrochloride was dissolved in water. The weak cation exchange resin was added to the drug solution in a weight ratio of fingolimod base to resin of about 1:8.96 and the dispersion was stirred for three hours. The dispersion was used to granulate crospovidone as the diluent in a suitable shear granulator. The granules were dried in a suitable dryer. The granules were encapsulated in hard gelatin capsules (fill weight 50 mg per capsule for 0.5 mg active strength).

Content Uniformity: The resulting composition was checked for content uniformity. The results are given in table 9 below:

TABLE 9

Results of the content uniformity of pharmaceutical composition of example 2

| Batch No | Assay values | Acceptance value (Limit: L1 ≤15 and L2 ≤25) |
|---|---|---|
| 1 | Mean 101.64%, Min: 97.63%, max: 105.55%, % RSD = 2.46 | 6.14 |

Table 9 is indicative of improved content uniformity with composition of example 2 as reflected by lower acceptance value, as compared to the composition of comparative example 1.

Stability Study: The pharmaceutical composition (capsules) of Example 2 were packed in AluAlu blister and were subjected to accelerated stability studies at various test conditions (40° C./75% RH, 30° C./65% RH; 25° C./60% RH). The samples were analyzed for assay of the drug and impurity levels at 3 Month and 6 Month. The results of the stability study are given in table 10 below

TABLE 10

Results of the chemical stability of pharmaceutical composition of example 2

| Parameters | Initial | 40/75% RH | | 30/65% RH | | 25/60% RH | |
|---|---|---|---|---|---|---|---|
| | | 3 M* | 6 M | 3 M | 6 M | 3 M | 6 M |
| Assay | 100.51 | 96.01 | 97.95 | 97.66 | 99.27 | 95.04 | 98.40 |
| Dissolution** at 45 mins | 84 | 81 | 84 | 78 | 79 | 77 | 80 |
| Impurity A | ND | 0.019 | 0.050 | 0.004 | 0.009 | 0.002 | 0.006 |
| Impurity B | ND | ND | ND | ND | ND | ND | ND |
| Impurity C | ND | ND | ND | ND | ND | ND | ND |
| % Highest unknown impurity | 0.083 | 0.190 | 0.242 | 0.073 | 0.127 | 0.073 | 0.087 |
| % Total impurity | 0.179 | 0.504 | 0.722 | 0.281 | 0.369 | 0.223 | 0.295 |
| Disintegration Time | 3.328 | 1.510 | 2.210 | 1.570 | 2.460 | 1.510 | 2.440 |
| Water Content | 10.425 | 11.559 | 12.919 | 11.126 | 1.189 | 10.569 | 12.416 |

*M = month
ND = not detectable;
**= USP Type II Apparatus (Paddle with sinkers) at 75 rpm, 500 ml of 0.1N Hydrochloric acid with 1% (w/v) Tween 80

It was observed that % total impurity observed after six months when the capsules were stored at 40° C./75% Relative Humidity, Were 1.39% and 3.2% for comparative example 1 and comparative example 2, respectively. In contrast, the total impurity at the end of three months for example 7 were about 0.5% which is significantly lower. Moreover, it was observed when capsules were stored for six months, the % total impurity increased nominally to 0.72% from 0.5% (refer to Table 10 above). Thus, it can be concluded that the pharmaceutical composition of Example 2 was much stable than the compositions without the weak acid cation exchange resin.

Example 3

The example illustrates a composition of the present invention comprising the ion-exchange resin of Formula 1, wherein X is hydrogen and ratio of fingolimod base to resin is 1:11.2 or ratio of fingolimod hydrochloride to resin is 1:10.

TABLE 11

Pharmaceutical composition using Amberlite IRP64; Fingolimod base to resin ratio is 1:11.2

| Sr. No. | Ingredients | mg/capsule | % w/w |
|---|---|---|---|
| | Step 1: Complexation | | |
| 1. | Fingolimod Hydrochloride equivalent to 0.5 mg Fingolimod base | 0.56 | 0.62% |
| 2 | Amberlite IRP 64 | 5.6 | 6.22% |
| 3 | Purified water | q.s. | |
| | Step 2: Granulation | | |
| 4 | Crospovidone | 43.84 | 48.71% |

TABLE 11-continued

Pharmaceutical composition using Amberlite IRP64; Fingolimod base to resin ratio is 1:11.2

| Sr. No. | Ingredients | mg/capsule | % w/w |
|---|---|---|---|
| | Step 3: Encapsulation | | |
| 1 | Hard Gelatin Capsule, Size "4" | 40.00 | 44.44% |

Procedure—Fingolimod hydrochloride was dissolved in water. The weak cation exchange resin was added to the drug solution (Fingolimod base to resin ratio of 1:11.2). The dispersion was stirred for three hours. The dispersion was used to granulate crospovidone as the diluent in a suitable shear granulator. The granules were then dried in a suitable dryer. The granules were encapsulated in hard gelatin capsules (fill weight 50 mg per capsule for 0.5 mg active strength).

Content Uniformity: The composition was checked for content uniformity. The results are given in Table 12 below.

TABLE 12

Results of the content uniformity of example 3

| Assay values | Acceptance value (Limit: L1 ≤15 and L2 ≤25) |
|---|---|
| Mean 98.12%, Min: 93.53%, max: 102.28%, % RSD = 2.42 | 6.07 |

Stability Studies: The capsules of Example 3 were packed in AluAlu blister and were subjected to accelerated stability studies at various test conditions (40° C./75% RH, 30° C./65% RH; 25° C./60% RH). The samples were analyzed for assay and impurity levels at 1 Month, 3 Month and 6 Month. The results of the stability study are given in table 13 below:

TABLE 13

Results of the chemical stability of pharmaceutical composition of example 3

| Parameters | Initial | 40/75% RH | | | 30/65% RH | | | 25/60% RH | | |
|---|---|---|---|---|---|---|---|---|---|---|
| | | 1 M* | 3 M | 6 M | 1 M | 3 M | 6 M | 1 M | 3 M | 6 M |
| Assay | 94.58 | 100.34 | 98.29 | 105.26 | 103.38 | 96.47 | 107.54 | 102.24 | 97.45 | 100.45 |
| Dissolution at** 45 mins | 77 | 80 | 76 | 78 | 76 | 74 | 72 | 90 | 78 | 73 |
| Impurity A | ND | ND | 0.004 | 0.022 | ND | ND | ND | ND | ND | ND |
| Impurity B | ND | ND | ND | ND | ND | ND | ND | ND | ND | ND |
| Impurity C | ND | ND | ND | ND | ND | ND | ND | ND | ND | ND |
| Highest unknown impurity | 0.084 | 0.071 | 0.066 | 0.092 | 0.072 | 0.068 | 0.066 | 0.072 | 0.071 | 0.066 |
| Total impurity | 0.150 | 0.256 | 0.315 | 0.496 | 0.210 | 0.266 | 0.228 | 0.205 | 0.196 | 0.220 |
| Disintegration time | 3.32 | 3.19 | 2.02 | 2.18 | 3.25 | 2.03 | 2.47 | 3.14 | 1.57 | 2.41 |
| Water Content | 9.57 | 10.83 | 11.22 | 10.782 | 10.75 | 11.55 | 10.747 | 10.94 | 10.29 | 9.882 |

*M = month

ND = not detectable;

**= USP Type II Apparatus (Paddle with sinkers) at 75 rpm, 500 ml of 0.1N Hydrochloric acid with 1% (w/v) Tween 80

It was observed that % total impurity observed after six months when the capsules were stored at 40° C./75% Relative Humidity, were 1.39% and 3.2% for comparative example 1 and comparative example 2, respectively. In contrast, the total impurity at the end of three months for example 3 were about 0.315% which is significantly lower. Thus, it can be concluded that the pharmaceutical composition of Example 3 was much stable than the compositions without the weak acid cation exchange resin.

Also an examination of % total impurities formed in Example 1 as compared to Example 3, it is seen that improved stability is seen when the proportion of resin (the ion-exchange resin of Formula 1, wherein X is hydrogen) is increased.

Example 4

The ion exchange complex of Fingolimod and the weak acid cation exchange resin present in the pharmaceutical composition of the present invention is given below in Table 14:

TABLE 14

Drug-resin complex of the present invention

| Sr. No. | Ingredients | mg/capsule | % w/w |
|---|---|---|---|
| | Step 1: Complexation | | |
| 1 | Fingolimod Hydrochloride equivalent to 0.5 mg Fingolimod base | 0.56 | 10% |
| 2 | Amberlite IRP 64 | 5.6 | 90% |
| 3 | Purified water | q.s. | |

Fingolimod hydrochloride was dissolved in water. The weak cation exchange resin was added to the drug solution at a Fingolimod hydrochloride to resin ratio of 1:10. The dispersion was stirred for three hours. The drug-resin complex was formed which was allowed to sediment. The sediment was kept aside for few hours.

Analysis of the free and complexed drug was then carried out. The supernatant obtained by the above method was filtered and analyzed for the free drug content. The sediment obtained above was dried and the drug-resin complex was analysed for the degree of complexation by following method of analysis.

To the specified amount of the drug complex was added 0.1 N HCl and the complexed drug was extracted in it by warming it at 37° C. and with intermediate shaking. Then a solvent system of acetonitile and methanol was added and the mixture was sonicated for about 20 minutes with intermittent shaking. The volume was appropriately made and filtered. The filtrate was used to further analyze the fingolimod hydrochloride by high performance liquid chromatography.

The percent of the drug complexed was found to be 99.46%. Thus, it can be concluded that the cation exchange resin, Amberlite IRP 64 was able to form an ion exchange complex with fingolimod hydrochloride substantially completely, when used in the Fingolimod hydrochloride to resin ratio of 1:10.

Example 5 (A-E)

Ion exchange resin complex of fingolimod hydrochloride and Amberlite IRP 64 at various ratios were prepared as per the Table 15 given below:

TABLE 15

Ion exchange complex of Fingolimod and Amberlite IRP64 at different ratios

| Ingredients | Example 5A | Example 5B | Example 5C | Example 5D | Example 5E |
|---|---|---|---|---|---|
| Ratio of Fingolimod base:Amberlite IRP 64 | 1:1.12 | 1:3.36 | 1:6.72 | 1:8.96 | 1:11.2 |
| Ratio of Fingolimod hydrochloride:Amberlite IRP 64 | 1:1 | 1:3 | 1:5 | 1:8 | 1:10 |
| Fingolimod Hydrochloride equivalent to 0.5 mg Fingolimod base | 0.56 | 0.56 | 0.56 | 0.56 | 0.56 |
| Amberlite IRP 64 | 0.56 | 1.68 | 3.36 | 4.48 | 5.6 |
| Purified water | q.s. | q.s. | q.s. | q.s. | q.s. |

Specified amount of Fingolimod hydrochloride as mentioned in the examples above was dissolved in sufficient water. Specified amounts of Amberlite IRP 64 were added. The resulting dispersion in each case was stirred well for 2 hours at ambient conditions. The resulting admixture was dried in rotavapor by applying vaccum and at temperature approximately 60° C. The admixtures so prepared were analyzed for the degree of complexation, wherein the percentage complexed drug; free drug and total drug were estimated by the method given below. The result of the complexation data has been given in table 16.

TABLE 16

Result of the percentage complexed drug, percentage free drug and total drug

| | Example 5 (A) | Example 5 (C) | Example 5 (D) | Example 5 (E) |
|---|---|---|---|---|
| % Complexed drug | 35.68 | 78.10 | 90.44 | 90.04 |
| % Free Drug | 56.88 | 26.42 | 14.22 | 5.51 |
| Total Drug | 93.88 | 112.77 | 112.17 | 101.3 |

Method of Estimation of Free Fingolimod:

Specified amount of the ion-exchange resin was transferred into a 200 ml volumetric flask. About 150 ml of water was added and the mixture was sonicated for about 20 min with intermittent shaking and the volume was made up to the mark with water. The admixture was mixed well and the whole 200 ml solution was centrifuged without wasting anything at 4000 rpm for 15 min. The clear supernatant contains the free drug (un-complexed non-resinate part). A sample of the supernatant was analyzed through a suitable HPLC method to obtain the free drug content. The residue part contains the complexed drug. To analyze the complexed drug, the sample was processed further as below:

Method of Estimation of Complexed Fingolimod:

The centrifuge tubes as obtained above were processed as below to determine the complexed drug content. The clear supernatant was carefully discarded. To ensure removal of the entire free drug content, about 10 ml of water was again added to the residue, and centrifugation was carried out at 4000 rpm for 15 mins. The clear supernatant was carefully discarded. The remaining residue is the ion-exchange complex containing the complexed drug. To analyze the complexed drug, 0.1 N Hydrochloric acid was added to the residue present in the tubes, the tubes were vortexed and heated in a water bath maintained at 37° C. for 30 mins. The liquid part of the tubes was collected in 200 ml volumetric flask. The tubes were washed at least twice with diluent mixture of buffer (potassium dihydrogen orthophosphate/orthophosphoric acid buffer) and acetonitrile in the ratio of 30:70 and the washings were collected into the same 200 ml volumetric flask. With intermittent shaking, the solution was sonicated for about 20 minutes. The solution was allowed to cool to room temperature and the volume was made up with the diluent as used above, followed by proper mixing and centrifugation at 4000 rpm for 15 min to get clear supernatant. This clear supernatant contains the complexed drug. A sample of the supernatant was analyzed through a suitable HPLC method to obtain the complexed drug content.

Method of Estimation of Total Fingolimod Content:

Specified amount of the ion-exchange was weighed accurately and transferred into a 200 ml volumetric flask. Measured volume of 0.1 N hydrochloric acid was added to this. The flask was heated into water bath maintained at 37° C. for about 30 min with intermittent shaking. The solution was then cooled and measured volume of diluent mixture of buffer (potassium dihydrogen orthophosphate/orthophosphoric acid buffer) and acetonitrile in the ratio of 30:70 was added followed by sonication for about 20 min with intermittent shaking. The volume up made up to the mark with diluent as above, mixed well and centrifuged at 4000 RPM for 15 minutes. The clear supernatant contains the total drug. A sample of the supernatant was analyzed through a suitable HPLC method to obtain the total drug content (as % of L.C.).

Example 6 (A-D)

Ion exchange resin complex of fingolimod hydrochloride and Amberlite IRP 88 at various ratios were prepared as per the Table 17 given below:

TABLE 17

Ion exchange complex of Fingolimod and Amberlite IRP88 at different ratios-

| Ingredients | Example 6A | Example 6B | Example 6C | Example 6D |
|---|---|---|---|---|
| Ratio of Fingolimod base:Amberlite IRP 88 | 1:1.12 | 1:6.72 | 1:8.96 | 1:11.2 |
| Ratio of Fingolimod hydrochloride:Amberlite IRP 88 | 1:1. | 1:6. | 1:8 | 1:10 |
| Fingolimod Hydrochloride equivalent to 0.5 mg Fingolimod base | 0.56 mg | 0.56 mg | 0.56 mg | 0.56 mg |
| Amberlite IRP 88 | 0.56 mg | 3.36 mg | 4.48 mg | 5.6 mg |
| Purified water | q.s. | q.s. | q.s. | q.s. |

Specified amount of Fingolimod Hydrochloride as mentioned in the examples above was dissolved in sufficient water. Specified amount of Amberlite IRP 88 was added. The resulting dispersion in each case was stirred well for 2 hours at ambient conditions. The resulting admixtures were dried by applying vacuum and temperature of approximately 60° C. The admixtures so prepared were analyzed for the degree of complexation, wherein the percentage complexed drug; free drug and total drug were estimated by following the method described in Example 5.

TABLE 18

Result of the percentage complexed drug, percentage free drug and total drug

| test | Example 6 (A) | Example 6 (C) |
|---|---|---|
| % Complexed drug | 86.38 | 95.82 |
| % Free Drug | 0.37 | 0.31 |
| Total | 99.69 | 100.69 |

Drug Resin Complex of Example 6(B) wherein the ratio of Fingolimod to Amberlite IRP 88 is 1:6.72, was subjected to accelerated stability study:

The drug-resin complex was subjected to accelerated stability studies at various test conditions (40° C./75% RH, 30° C./65% RH; 25° C./60% RH). The samples were analyzed for assay, impurity levels at 1 Month, 2 Month and 3 Month. The stability data of the drug-resin complex of Example 6(B) is presented below in table 19:

TABLE 19

Stability data of the drug-resin complex at 1:6.72 ratio

| Condition/test | Initial | 40° C./75% Relative humidity | | | 30°/65% Relative humidity | | | 25°/60% Relative humidity | | |
|---|---|---|---|---|---|---|---|---|---|---|
| | | 1 M* | 2 M | 3 M | 1 M | 2 M | 3 M | 1 M | 2 M | 3 M |
| Assay | 106.17 | 96.54 | 96.18 | 102.67 | 98.23 | 97.67 | 103.21 | 99.54 | 97.52 | 100.44 |
| Impurity A | ND | ND | ND | ND | ND | ND | ND | ND | ND | ND |
| % Highest unknown Impurity | 0.061 | 0.185 | 0.056 | 0.062 | 0.176 | 0.056 | 0.060 | 0.173 | 0.057 | 0.057 |
| % Total impurity | 0.149 | 0.185 | 0.115 | 0.148 | 0.176 | 0.119 | 0.155 | 0.173 | 0.118 | 0.139 |

*M = month

Example 7

The example illustrates a composition of the present invention comprising the ion-exchange resin of Formula 1, wherein X is potassium and ratio of fingolimod base to resin is 1:6.72 or ratio of fingolimod hydrochloride to resin is 1:6.

TABLE 20

Pharmaceutical composition of the present invention using Amberlite IRP88

| Sr. No. | Ingredients | mg/capsule | % w/w |
| --- | --- | --- | --- |
| 1 | Fingolimod Hydrochloride equivalent to 0.5 mg Fingolimod base | 0.56 | 0.59 |
| 2 | Amberlite IRP 88 | 3.36 | 3.54 |
| 4 | crospovidone | 49.98 | 52.61 |
| 5 | colloidal silicon dioxide | 0.55 | 0.58 |
| 6 | Magnesium stearate | 0.55 | 0.58 |
| 7 | Hard gelatin Capsule, Size '4' | 40.00 | 42.10 |

Specified amount of Fingolimod Hydrochloride was dissolved in sufficient water. 3.36 mg of the weak cation exchange resin—Amberlite IRP 88 was added. The resulting dispersion was stirred well for 2 hours at ambient conditions. The resulting admixture was dried by applying vacuum at temperature approximately 60° C. Equivalent amount of the dried admixture were taken and mixed with crospovidone and colloidal silicon dioxide and blended for 45 minutes. The blend so obtained was lubricated with magnesium stearate. The lubricated blend was filled into hard gelatin capsules.

The content uniformity of the capsules of Example 7 were checked as per the USP method. The results are given in Table 21 below.

TABLE 21

Results of the content uniformity of capsules of Example 7

| Assay values | Acceptance value (Limit: L1 ≤15 and L2 ≤25) |
| --- | --- |
| Mean 98.12%, Min: 93.53%, max: 102.28%, % RSD = 2.42 | 5.22 |

The capsules of Example 7 were packed in Aluminum/Aluminum blister pack. It was subjected to accelerated stability testing at various test conditions (40° C./75% RH, 30° C./65% RH; 25° C./60% RH). The results of the stability study are given in table 22 below:

TABLE 22

Stability data of the pharmaceutical composition comprising ion-exchange resin complex:

| Condition/test | Initial | 40° C./75% Relative humidity | | | 30°/65% Relative humidity | | | 25°/60% Relative humidity | | |
| --- | --- | --- | --- | --- | --- | --- | --- | --- | --- | --- |
| | | 1 M* | 2 M | 3 M | 1 M | 2 M | 3 M | 1 M | 2 M | 3 M |
| Assay | 99.91 | 101.07 | 100.33 | 95.67 | 97.80 | 101.15 | 95.78 | 97.25 | 101.67 | 96.10 |
| Impurity A | ND | ND | ND | 0.066 | ND | ND | ND | ND | ND | ND |
| % Highest unknown Impurity | 0.082 | 0.198 | 0.196 | 0.085 | 0.192 | 0.194 | 0.066 | 0.205 | 0.195 | 0.066 |
| % Total impurity | 0.351 | 0.488 | 0.563 | 0.249 | 0.368 | 0.404 | 0.152 | 0.384 | 0.386 | 0.283 |

M = months

It was observed that % total impurity observed after six months when the capsules were stored at 40° C./75% Relative Humidity, Were 1.39% and 3.2% for comparative example 1 and comparative example 2, respectively. In contrast, the total impurity at the end of three months for example 7 were about 0.248% which is significantly lower. Thus, it can be concluded that the pharmaceutical composition of Example 7 was much stable than the compositions without the weak acid cation exchange resin.

Also an examination of % total impurities formed in Example 2 as compared to Example 7, it is seen that improved stability is seen when the proportion of resin (the ion-exchange resin of Formula 1, wherein X is potassium) is increased.

The invention claimed is:

1. A pharmaceutical composition comprising fingolimod and a weak acid cation exchange resin in the form of an ion-exchange complex and pharmaceutically acceptable excipients, wherein the weak acid cation exchange resin is a copolymer of methacrylic acid and divinylbenzene as depicted by Formula I:

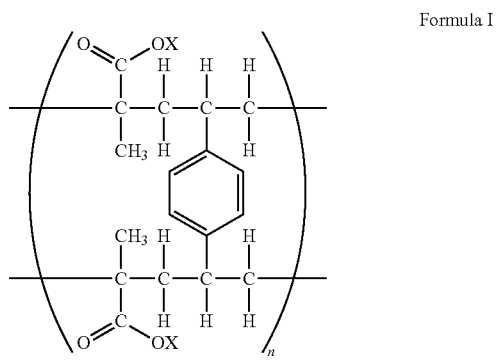

Formula I wherein X is hydrogen or an inorganic monovalent cation, the pharmaceutical composition prepared by a process comprising the steps of:
  a) forming an ion-exchange complex of fingolimod with the weak acid cation exchange resin; and
  b) mixing the ion-exchange complex with a pharmaceutically acceptable excipient,
wherein the weight ratio of fingolimod to the weak acid cation exchange resin is about 1:6 by weight.

2. The pharmaceutical composition as claimed in claim 1, wherein X is hydrogen and the weak acid cation exchange resin has an ion exchange capacity of not less than 10.0 meq/g on dried basis, wherein the mean particle size of the resin particles lies in the range of 150 micron to 45 micron and wherein the particle size distribution of the resin is such that not more than 70% of particles have a particle size greater than 50 micron; 15% to 30% of the particles have a particle size of greater than 75 micron and not more than 1% of the particles have a particle size of greater than 150 micron.

3. The pharmaceutical composition as claimed in claim 1, wherein X is potassium and wherein the weak acid cation exchange resin is such that the mean particle size of the resin particles lies in the range of 150 micron to 45 micron and wherein the particle size distribution of the resin is such that not more than 30% of the particles have a particle size in the range of 75 micron to 150 micron; not more than 1% of the particles have a particle size of greater than 150 micron.

4. A pharmaceutical composition comprising fingolimod and a weak acid cation exchange resin in the form of an ion-exchange complex and pharmaceutically acceptable excipients, wherein the weak acid cation exchange resin is a copolymer of methacrylic acid and divinylbenzene as depicted by Formula I:

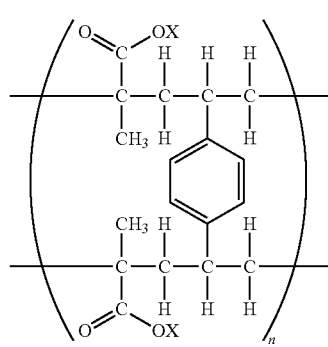

Formula I wherein X is hydrogen or an inorganic monovalent cation, the pharmaceutical composition prepared by a process comprising the steps of:
  a) dissolving fingolimod in the form of its salt in water;
  b) adding the weak acid cation exchange resin exchange resin and obtaining a suspension;
  c) adding the suspension obtained in b) to pharmaceutically acceptable excipients to form granules; and
  d) drying the granules and converting them into a solid dosage form,
wherein the weight ratio of fingolimod to the weak acid cation exchange resin is about 1:6 by weight.

5. The pharmaceutical composition as claimed in claim 4, wherein X is hydrogen and the weak acid cation exchange resin has an ion exchange capacity of not less than 10.0 meq/g on dried basis, wherein the mean particle size of the resin particles lies in the range of 150 micron to 45 micron and wherein the particle size distribution of the resin is such that not more than 70% of particles have a particle size greater than 50 micron; 15% to 30% of the particles have a particle size of greater than 75 micron and not more than 1% of the particles have a particle size of greater than 150 micron.

6. The pharmaceutical composition as claimed in claim 4, wherein X is potassium and wherein the weak acid cation exchange resin is such that the mean particle size of the resin particles lies in the range of 150 micron to 45 micron and wherein the particle size distribution of the resin is such that not more than 30% of the particles have a particle size in the range of 75 micron to 150 micron; not more than 1% of the particles have a particle size of greater than 150 micron.

7. A process for preparing the pharmaceutical composition of claim 1, comprising the steps of:
  a) forming an ion-exchange complex of fingolimod with the weak acid cation exchange resin; and
  b) mixing the ion-exchange complex with a pharmaceutically acceptable excipient.

8. The process as claimed in claim 7, wherein X is hydrogen and the weak acid cation exchange resin has an ion exchange capacity of not less than 10.0 meq/g on dried basis, wherein the mean particle size of the resin particles lies in the range of 150 micron to 45 micron and wherein the particle size distribution of the resin is such that not more than 70% of particles have a particle size greater than 50 micron; 15% to 30% of the particles have a particle size of greater than 75 micron and not more than 1% of the particles have a particle size of greater than 150 micron.

9. The process as claimed in claim 7, wherein X is potassium and wherein the weak acid cation exchange resin is such that the mean particle size of the resin particles lies in the range of 150 micron to 45 micron and wherein the particle size distribution of the resin is such that not more than 30% of the particles have a particle size in the range of 75 micron to 150 micron; not more than 1% of the particles have a particle size of greater than 150 micron.

10. A process for preparing the pharmaceutical composition of claim 1, comprising the steps of:
  a) dissolving fingolimod in the form of its salt in water;
  b) adding the weak acid cation exchange resin exchange resin and obtaining a suspension;
  c) adding the suspension obtained in b) to pharmaceutically acceptable excipients to form granules; and
  d) drying the granules and converting them into a solid dosage form.

11. The process as claimed in claim 10, wherein X is hydrogen and the weak acid cation exchange resin has an ion exchange capacity of not less than 10.0 meq/g on dried basis, wherein the mean particle size of the resin particles lies in the range of 150 micron to 45 micron and wherein the particle size distribution of the resin is such that not more than 70% of particles have a particle size greater than 50 micron; 15% to 30% of the particles have a particle size of greater than 75 micron and not more than 1% of the particles have a particle size of greater than 150 micron.

12. The process as claimed in claim 10, wherein X is potassium and wherein the weak acid cation exchange resin is such that the mean particle size of the resin particles lies in the range of 150 micron to 45 micron and wherein the particle size distribution of the resin is such that not more than 30% of the particles have a particle size in the range of 75 micron to 150 micron; not more than 1% of the particles have a particle size of greater than 150 micron.

13. The process as claimed in claim 10, wherein the solid dosage form is a bilayered tablet.

* * * * *